United States Patent [19]

Mishra et al.

[11] Patent Number: 4,880,828

[45] Date of Patent: Nov. 14, 1989

[54] 2-(TETRAHYDRO-2-THIENYL)PHENYL ESTERS OF PHOSPHOROTHIOIC ACID

[75] Inventors: Anupama Mishra, Guelph, Canada; Richard C. Moore, Wallingford, Conn.

[73] Assignees: Uniroyal Chemical, Inc., Middlebury, Conn.; Uniroyal Chemical Ltd./Ltee, Don Mills, Canada

[21] Appl. No.: 149,774

[22] Filed: Jan. 29, 1988

[51] Int. Cl.$^4$ .............. A61K 31/38; C07D 333/46
[52] U.S. Cl. ............................ 514/438; 514/446; 549/6; 549/8
[58] Field of Search .............. 549/6.8; 514/438, 446

[56] References Cited

U.S. PATENT DOCUMENTS

| | | | |
|---|---|---|---|
| 2,599,516 | 6/1952 | Moyle | 558/212 |
| 2,761,806 | 9/1956 | Boyer | 558/210 |
| 2,769,013 | 10/1956 | Lowenstein-Lom | 549/6 |
| 3,042,703 | 7/1962 | Schegk et al. | 558/196 |
| 3,275,718 | 9/1966 | Sehring et al. | 558/212 |
| 3,468,984 | 9/1969 | Beriger | 558/212 |
| 3,600,444 | 8/1971 | Dachs | 558/197 |
| 3,600,472 | 9/1971 | Sehring et al. | 558/197 |
| 4,268,506 | 5/1981 | Baumann et al. | 514/95 |
| 4,461,764 | 7/1984 | Magee | 549/6 |

*Primary Examiner*—Mary C. Lee
*Assistant Examiner*—Zinna Northington
*Attorney, Agent, or Firm*—John A. Shedden

[57] ABSTRACT

A new class of 2-(tetrahydro-2-thienyl)phenyl esters of phosphorothioic acid is disclosed. This class of compounds is an effective pesticide and finds particular application as an insecticide. A class of pesticidal compositions employing these compounds in combination with a carrier therefor is also set forth.

13 Claims, No Drawings

2-(TETRAHYDRO-2-THIENYL)PHENYL ESTERS OF PHOSPHOROTHIOIC ACID

BACKGROUND OF THE INVENTION

1. Field of the Invention

The present invention is directed to a new class of 2-(tetrahydro-2-thienyl)phenyl esters of phosphorothioic acid. More particularly, the instant invention is directed to a class of 2-(tetrahydro-2-thienyl)phenyl esters of phosphorothioic acid useful as insecticides.

2. Background of the Prior Art

The devastation caused by pests represents a serious economical threat to commercially important food, fiber and ornamental plants. Particularly serious is the attack of pests against important grain plants such as corn and rice. For this reason the development of new, more effective pesticides represents an ongoing scientific activity. It is particularly important to develop pesticides effective at very low dosages. Such pesticides provide necessary control without attendant environmental difficulties.

Esters of phosphorothioic acids, that is, phosphorothioates, are well known in the art. Several disclosures of these esters, which allege insecticidal, acaricidal and/or nematocidal utility, are available in the art. For example, U.S. Pat. No. 2,599,516 issued to Moyle discloses O,O-dimethyl or O,O-diethyl O-2,4,5-trichlorophenyl phosphorothioates. These compounds are said to possess systemic insecticidal properties and provide effective control of flies and other household pests.

U.S. Pat. No. 2,761,806 issued to Boyer sets forth a class of O-chloro-substituted phenyl O,O-dialkyl phosphorothioates useful as non-systemic nematocides. These phosphorothioates are alleged to also be effective as soil insecticides.

U.S. Pat. No. 3,042,703 issued to Schegk et al. is of particular interest, directed as it is to a class of thiophosphoric acid esters. The species, O,O-dialkyl O-4-(methylthio or methylsulfinyl)phenyl phosphorothioate, is useful as an insecticide and particularly as a nematocide, active against free-living, cyst-forming and root-knot nematodes.

Another class of non-systemic insecticides are the O-(4-bromo-2,5-dichlorophenyl) O,O-dialkyl phosphorothioates described in U.S. Pat. No. 3,275,718 issued to Sehring et al.

The compound O,O,O',O'-tetramethyl O,O'-thiodi-p-phenylene phosphorothioate is the subject of U.S. Pat. No. 3,217,636 issued to Lovell et al. This compound is recited, in the '636 patent, to be effective in controlling cutworms, thrips on citrus and Lygus bugs.

Another class of phosphoric and phosphonic acid esters are recited to be useful as insecticides, fungicides, acaricides, nematocides and molluscicides. This class of esters is taught in U.S. Pat. No. 3,468,984 issued to Beriger. The '984 patent particularly discloses O-2,5-dichloro-4-iodophenyl O,O-dimethyl phosphorothioate as a non-systemic contact and stomach insecticide and acaricide.

Finally, U.S. Pat. No. 3,600,472 issued to Sehring et al. describes O-(2,5-dichloro-4-alkylmercaptophenyl)-phosphorothioates and analogous phosphorothioates useful as insecticides and acaricides. Particularly interesting is the compound, O-2,5-dichloro-4-(methylthio)-phenyl O,O-diethyl phosphorothioate.

All of the phosphorothioates described in the above references having pesticidal activity are structurally distinguished from esters of 2-(tetrahydro-2-thienyl)-phenyl phosphorothioic acid.

The above remarks establish the absence in the art of an important class of pesticides, the esters of 2-(tetrahydro-2-thienyl)phenyl phosphorothioic acid.

BRIEF SUMMARY OF THE INVENTION

The present invention is directed to a new important class of 2-(tetrahydro-2-thienyl)phenyl esters of phosphorothioic acid. This new class of compounds find important utility as effective pesticides.

In accordance with the present invention a new class of compounds having the structural formula

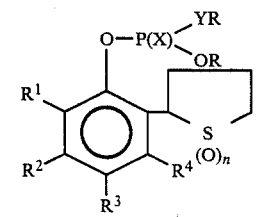

where

R is $C_1$-$C_6$ alkyl;

$R^1$-$R^4$ are the same or different and are hydrogen, halogen, nitro, $C_1$-$C_8$ alkyl, $C_1$-$C_2$ haloalkyl, $C_5$-$C_6$ cycloalkyl, $C_7$-$C_9$ aralkyl, phenyl, $C_1$-$C_6$ alkoxy, $C_1$-$C_6$ alkylthio, $C_1$-$C_6$ alkylsulfinyl, $C_1$-$C_6$ alkylsulfonyl, $C_7$-$C_9$ aralkoxy, phenoxy, phenylthio, phenylsulfinyl, phenylsulfonyl, tetrahydro-2-thienyl, dioxytetrahydro-2-thienyl, alkali metal carboxylate, $C_2$-$C_5$ alkoxycarbonyl, phenoxycarbonyl or $N(R^5,R^6)$;

$R^5$ and $R^6$ are the same or different and are hydrogen or $C_1$-$C_2$ alkyl;

X and Y are the same or different and are oxygen or sulfur; and n is 0, 1 or 2.

In another embodiment of the present invention a pesticidal composition comprising the above-defined compound and a carrier therefor is disclosed.

In yet another embodiment to the present invention, a method for controlling pests is described. In this method a pesticidally effective amount of the above-recited compounds is applied to the locus to be protected.

Finally, in still another embodiment of the instant invention, a process for forming the above compound is taught. In this process a compound having the structural formula

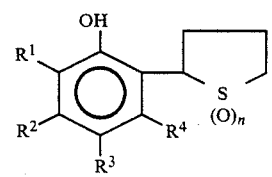

where $R^1$, $R^2$, $R^3$, $R^4$, $R^5$, $R^6$ and n have the meanings given for the compound of the present invention is reacted with a dialkyl halothiophosphate.

DETAILED DESCRIPTION OF THE INVENTION

The 2-(tetrahydro-2-thienyl)phenyl esters of phosphorothioic acid of the present invention have the structural formula

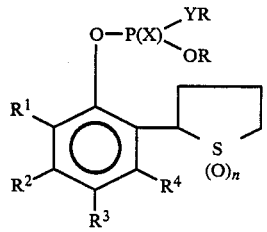

where
  R is $C_1$–$C_6$ alkyl;
  $R^1$ to $R^4$ are the same or different and are hydrogen, halogen, nitro, $C_1$–$C_8$ alkyl, $C_1$–$C_2$ haloalkyl, $C_5$–$C_6$ cycloalkyl, $C_7$–$C_9$ aralkyl, phenyl, $C_1$–$C_6$ alkoxy, $C_1$–$C_6$ alkylthio, $C_1$–$C_6$ alkylsulfinyl, $C_1$–$C_6$ alkylsulfonyl, $C_7$–$C_9$ aralkoxy, phenoxy, phenylthio, phenylsulfinyl, phenylsulfonyl, tetrahydro-2-thienyl, dioxytetrahydro-2-thienyl, alkali metal carboxylate, $C_2$–$C_5$ alkoxycarbonyl, phenoxycarbonyl or $N(R^5,R^6)$;
  $R^5$ and $R^6$ are the same or different and are hydrogen or $C_1$–$C_2$ alkyl;
  X and Y are the same or different and are oxygen or sulfur; and
  n is 0, 1 or 2.

More preferably, the compound of the present invention has the structural formula (I) where
  R is $C_1$–$C_2$ alkyl;
  $R^1$ is hydrogen, $C_1$–$C_6$ alkoxy, $C_2$–$C_5$ alkoxycarbonyl, phenyl, tetrahydro-2-thienyl, dioxotetrahydro-2-thienyl or chlorine;
  $R^2$ is hydrogen or methyl;
  $R^3$ is hydrogen methyl, ethyl, isopropyl, methoxy, isopropyloxy, nitro, chlorine, methylthio, methylsulfinyl, methylsulfonyl or phenyl;
  $R^4$ is hydrogen or methyl;
  X is sulfur;
  Y is oxygen; and
  n is 0 or 2.

Most preferably, compounds of the present invention have the structural formula (I) where
  R is ethyl;
  $R^1$ is hydrogen or chlorine;
  $R^2$ is hydrogen or methyl;
  $R^3$ is nitro, chlorine, methyl, methylthio, methoxy, methylsulfinyl or methylsulfonyl;
  $R^4$ is hydrogen or methyl; and
  X is sulfur;
  Y is oxygen; and
  n is 0 or 2.

In another aspect of the present invention a process is provided for making compounds having the structural formula (I). In this process a compound having the structural formula

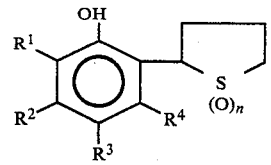

where $R^1$, $R^2$, $R^3$, $R^4$, $R^5$, $R^6$ and n have the meanings given for the compound having the structural formula (I) is reacted with a dialkylhalothiophosphate. This reaction preferably occurs in the presence of a polar solvent and a neutralizing base.

It is particularly preferred that the dialkylhalo-thiophosphate be $C_1$–$C_2$ dialkylchlorothiophosphate. Moreover, the polar solvent is preferably methyl ethyl ketone, acetone or acetonitrile. The neutralizing base is preferably insoluble in the polar solvent. A preferred base meeting this criterion is anhydrous potassium carbonate.

In the preferred embodiment wherein the S-oxide or S,S-dioxide is synthesized, the corresponding thio compound, that is, the compound formed in the above procedure where n is 0, is reacted with hydrogen peroxide in the presence of water and a suitable catalyst, preferably sodium tungstate, in accordance with methods well known in the art.

It is noted that the compounds having the structural formula (II), the phenol compound reacted to form the compounds of the present invention having the structural formula (I), are themselves novel. These compounds are formed by reacting phenol or a substituted phenol having the structural formula

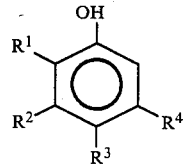

where $R^1$, $R^2$, $R^3$, $R^4$, $R^5$ and $R^6$ have the meanings given for the compound having the structural formula (I) with tetrahydrothiophene. This reaction occurs at low temperature, preferably between 0° C. and −70° C. The reaction is preferably conducted in solution in the presence of N-chlorosuccinimide and triethylamine. The preferred solvent is methylene chloride.

The compounds having the structural formula (I) have utility as pesticides. Thus, the compounds of this invention are utilized in pesticidal compositions. These pesticidal compositions comprise a pesticidally effective amount of a compound having the structural formula (I), where R, $R^1$, $R^2$, $R^3$, $R^4$, $R^5$, $R^6$, X, Y and n have the most general meanings of the compound whose structural formula is (I), and a carrier therefor.

More preferably, a pesticidal composition is provided which comprises a pesticidally effective amount of a compound having the structural formula (I), where R, $R^1$, $R^2$, $R^3$, $R^4$, X, Y and n have the meanings for the preferred embodiment of the compound of the present invention, and a carrier therefor.

Still more preferably, the pesticidal composition of this invention comprises a compound having the structural formula (I) where R, $R^1$, $R^2$, $R^3$, $R^4$, X, Y and n have the meanings given for the most preferred group of compounds having structural formula (I) and a carrier therefor.

The pesticidal compositions of the present invention may be insecticidal, nematocidal or acaricidal compositions. That is, insecticidal, nematocidal and acaricidal compositions comprise the identical compounds employed in the pesticidal composition with a carrier therefor, except that the amount of that compound is an insecticidally, nematocidally and acaricidally effective amount rather than a pesticidally effective amount. The preferred and more preferred insecticidal, nematocidal and acaricidal compositions coincide with the preferred and more preferred pesticides, respectively. That is, the preferred and more preferred insecticidal, nematocidal and acaricidal compositions include the identical compounds having the structural formula (I) as employed in the preferred and more preferred pesticidal compositions, respectively.

The pesticidal compositions of the present invention, as stated above, employ compounds having the structural formula (I) in combination with a carrier. The carrier, within the contemplation of the composition of this invention, may be a finely divided or granular organic or inorganic inert material. Among the inert carriers within the contemplation of this invention are attapulgate clay, sand, vermiculite, corncobs, activated carbon and mineral silicates such a mica, talc, pyrophyllite and clays.

In another preferred embodiment of the composition of this invention, the composition comprises a solution. That is, the active agent, a compound whose structural formula is (I), is dissolved in a suitable solvent which acts as the carrier. Among the solvents, acting as carrier, within the contemplation of this invention are acetone, methanol, isopropanol, t-butyl alcohol, cyclohexanol, n-butyl alcohol, cyclohexanone, toluene, xylene, dioxane, dimethylformamide, dimethylsulfoxide, ethylene dichloride and N-methylpyrrolidone.

In still another preferred embodiment of the composition of the present invention, the carrier of the composition is a water emulsion. The emulsion is prepared from a solution as described immediately above. To the solution is added a surface active agent. Surface active agents suitable for use in forming the emulsion of this invention are known to those skilled in the art. McCutcheon's Detergents and Emulsifiers, Allured Publishing Corp., Ridgewood, N.J. (1970); U.S. Patent 2,514,916, Columns 2 to 4; and U.S. Pat. No. 2,547,734, Columns 3 and 4, provide detailed examples of such surface active agents. These agents may be anionic, non-ionic or cationic.

In yet still another preferred embodiment of the composition of this invention, the composition employs a dispersant as carrier. In this embodiment the active insecticidal agent, a compound whose structural formula is (I), is mixed with a solvent of the type described above to form a solution which is added to one of the above-described surface active agents in water.

In even still another embodiment of the composition of the instant invention the active compound is premixed with an inert solid carrier which is added to a surface active agent and water to provide another form of dispersion within the contemplation of the composition of this invention.

The embodiment discussed immediately above, the disposition of the active agent on a solid inert carrier, which is dispersed in a liquid to form a dispersion, may alternatively be employed in a non-liquid form. That is, the composition of this invention may take the form of a dust, granules, a paste or a wettable powder. In these embodiments the active compound of this invention, the compound having the structural formula (I), is admixed with the inert carrier to form a solid composition. Thus, for example, in the embodiment wherein a powder is formed, the solid inert carrier is provided in powdered form. In many such cases the inert carrier is a mineral silicate. The solid may then be made wettable by the addition of a surface active agent, well known to those skilled in the art, referred to in the above-recited references directed to surface active agents.

In another principal application of the composition of this invention the carrier is an aerosol. To prepare the aerosol composition the active compound having the structural formula (I) is dissolved in a first solvent. This first solvent is conventional in the sense that although the first solvent is volatile, it is not highly volatile. The solution is then admixed with a highly volatile solvent, a so-called liquid aerosol carrier. The aerosol carrier is liquid only under elevated pressure. At ordinary temperatures at atmospheric pressure the aerosol carrier is a gas. In a subembodiment of this preferred embodiment the aerosol carrier may itself be active. For example, the carrier may be a fungicide, a herbicide, a bacteriacide or a plant growth regulant.

In another aspect of the present invention a method is provided for controlling pests wherein a pesticidally effective amount of a compound having the structural formula (I), where R, $R^1$, $R^2$, $R^3$, $R^4$, $R^5$, $R^6$, X, Y and n have the meanings given for the compound of the present invention is applied to the locus to be protected.

More preferably, the method for controlling pests, comprising applying to the locus to be protected an insecticidally effective amount of a compound having the structural formula (I), entails use of a compound within the contemplation of structural formula (I), where R, $R^1$, $R^2$, $R^3$, $R^4$, X, Y and n have the meanings given for the preferred compounds of structural formula (I) of the present invention.

Still more preferably, the method for controlling pests includes the application of an insecticidally effective amount of a compound having the structural formula (I), where R, $R^1$, $R^2$, $R^3$, $R^4$, X, Y and n have the meanings given for the most preferred compounds of the present invention to the locus to be protected.

It is emphasized that the method of controlling pests of this invention may be effectuated by either foliar and systemic means.

As in the case of the pesticidal compositions wherein the pesticidal composition may be insecticidal, nematocidal or acaricidal, so too the method of controlling pests may, more specifically, take the form of controlling insects, nematodes or acarids. Again, as in the case of the compositions of this invention, the method, the preferred method and the more preferred method of controlling pests in the present invention coincide with the method of controlling insects, nematodes and acarids. That is, the identification of the compounds used to control pests is identical to the compounds employed to control insects, nematodes and acarids. Similarly, the compounds used to control pests in the preferred and more preferred methods coincide with those utilized in the preferred and more preferred methods of control of pests. The only difference in each case is that whereas a pesticidally effective amount is applied in the method of controlling pests, an insecticidally effective amount, a nematocidally effective amount or an acaricidally effective amount are utilized in the method of controlling insects, nematodes or acarids, respectively.

Among the insects controlled by the compound of the present invention, the control of corn rootworm and rice planthopper are particularly important. Of the acarids, control of mites by the compound of this invention is paramount.

The following examples are given to illustrate the scope of the present invention. Because these examples are given for illustrative purposes only, the invention embodied herein should not be limited to the actual examples provided.

EXAMPLE 1

Preparation of O,O-Diethyl O-2-(Tetrahydro-2-Thienyl)Phenyl Phosphorothioate (Compound No. 1)

A mixture of 3 g. of 2-(tetrahydro-2-thienyl) phenol, 4 g. of diethylchlorothiophosphate, 50 ml. of methyl ethyl ketone and 10 g. of anhydrous potassium carbonate was refluxed for 5 hours. Thereafter, the solids were recovered by filtration and the solvent was removed. The residue was treated with ether and water resulting in the formation of a two-layer liquid. The water layer was removed and the ether layer was washed twice with water. The ether layer resulting therefrom was dried over magnesium sulfate and the solvent removed.

Three grams of an oil, O,O-diethyl O-2-(tetrahydro-2-thienyl)phenyl phosphorothionate, was obtained.

NMR(CDCl$_3$) δ1.35(t,6H); δ2.2(m,4H); δ3.0(m,2H) δ4.3(q,4H); δ4.85(t,1H); δ7.2(m,3H), δ7.7(m,1H)

EXAMPLE 2

Preparation of Compound Nos. 2–34

Additional compounds (nos. 2–34) were prepared following the procedure set forth in Example 1. These compounds were all defined by structural formula (I).

The compounds 2–34 were obtained as oils at ambient temperature. They were characterized by their NMR (Nuclear Magnetic Resonance) spectra, as given in Table 2. These structures were further confirmed by their IR (Infrared) spectra showing the disappearance of the hydroxyl group present in the starting phenolic materials.

TABLE 1

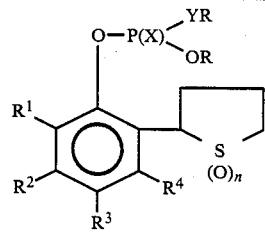

| Compound No. | R | R$^1$ | R$^2$ | R$^3$ | R$^4$ | X | Y | n |
|---|---|---|---|---|---|---|---|---|
| 1 | C$_2$H$_5$ | H | H | H | H | S | O | 0 |
| 2 | C$_2$H$_5$ | H | H | H | H | S | O | 2 |
| 3 | C$_2$H$_5$ | H | CH$_3$ | H | CH$_3$ | S | O | 0 |
| 4 | C$_2$H$_5$ | H | H | CH$_3$ | H | S | O | 0 |
| 5 | C$_2$H$_5$ | H | H | NO$_2$ | H | S | O | 0 |
| 6 | C$_2$H$_5$ | H | H | Cl | H | S | O | 0 |
| 7 | C$_2$H$_5$ | H | H | Cl | H | S | O | 2 |
| 8 | C$_2$H$_5$ | Cl | H | Cl | H | S | O | 0 |
| 9 | C$_2$H$_5$ | H | H | CH$_3$ | H | S | O | 2 |
| 10 | C$_2$H$_5$ | H | H | SCH$_3$ | H | S | O | 0 |
| 11 | C$_2$H$_5$ | H | H | SO$_2$CH$_3$ | H | S | O | 2 |
| 12 | C$_2$H$_5$ | H | H | SO$_2$CH$_3$ | H | S | O | 0 |
| 13 | C$_2$H$_5$ | H | H | SO$_2$CH$_3$ | H | S | O | 0 |
| 14 | C$_2$H$_5$ | H | H | C$_2$H$_5$ | H | S | O | 0 |
| 15 | C$_2$H$_5$ | H | H | CH(CH$_3$)$_2$ | H | S | O | 0 |
| 16 | C$_2$H$_5$ | H | H | C$_2$H$_5$ | H | S | O | 2 |
| 17 | C$_2$H$_5$ | H | H | C(CH$_3$)$_3$ | H | S | O | 2 |
| 18 | C$_2$H$_5$ | H | H | C(CH$_3$)$_3$ | H | S | O | 0 |
| 19 | C$_2$H$_5$ | H | H | H | H | S | O | 1 |
| 20 | C$_2$H$_5$ | H | H | CH$_3$ | H | S | O | 1 |
| 21 | C$_2$H$_5$ | H | CH$_3$ | H | H | S | O | 0 |
| 22 | C$_2$H$_5$ | H | H | H | CH$_3$ | S | O | 0 |
| 23 | C$_2$H$_5$ | H | H | C$_2$H$_5$ | H | S | O | 1 |
| 24 | C$_2$H$_5$ | H | H | CH(CH$_3$)$_2$ | H | S | O | 1 |
| 25 | C$_2$H$_5$ | OCH(CH$_3$)$_2$ | H | H | H | S | O | 0 |
| 26 | C$_2$H$_5$ | OCH(CH$_3$)$_2$ | H | H | H | S | O | 2 |
| 27 | C$_2$H$_5$ | C$_6$H$_5$ | H | H | H | S | O | 0 |
| 28 | C$_2$H$_5$ | C$_6$H$_5$ | H | H | H | S | O | 2 |
| 29 | C$_2$H$_5$ | COOCH$_3$ | H | H | H | S | O | 0 |
| 30 | C$_2$H$_5$ | tetrahydro-2-thienyl | H | H | H | S | O | 0 |
| 31 | C$_2$H$_5$ | H | H | OCH$_3$ | H | S | O | 0 |
| 32 | C$_2$H$_5$ | tetrahydro-2-thienyl | H | OCH$_3$ | H | S | O | 0 |
| 33 | C$_2$H$_5$ | tetrahydro-2-thienyl | H | SCH$_3$ | H, | S | O | 0 |
| 34 | C$_2$H$_5$ | dioxy-tetrahydro- | H | SO$_2$CH$_3$ | H | S | O | 2 |

TABLE 1-continued

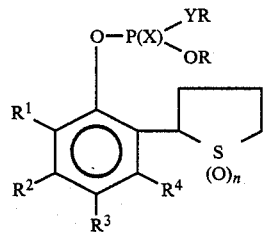

| Compound No. | R | R¹ | R² | R³ | R⁴ | X | Y | n |
|---|---|---|---|---|---|---|---|---|
| | 2-thienyl | | | | | | | |

TABLE 2

| Compound No. | NMR CHARACTERISTICS |
|---|---|
| 2 | t(6)1.35; m(4)2.40; m(2)3.2; m(4)4.3; m(1)4.9; m(4)7.0–7.5 |
| 3 | t(6)1.35; m(12)2.2–2.5; m(4)4.3; t(1)5.1; s(1)6.9; s(1)7.1 |
| 4 | t(6)1.40; m(9)1.8–2.5; m(4)4.3; t(1)4.9; m(3)6.8–7.5 |
| 5 | t(6)1.40; m(4)2.2; m(2)3.1; m(4)4.3; t(1)4.9; m(3)7.2–8.8 |
| 6 | t(6)1.40; m(4)2.1; m(2)3.0; m(4)4.25; t(1)4.8; m(2)7.1; m(1)7.6 |
| 7 | t(6)1.40; m(4)2.4; m(2)3.2; m(5)4.3; m(3)7.3 |
| 8 | t(6)1.40; m(4)2.2; m(2)3.6; m(4)4.3; t(1)4.9; m(2)7.1–7.8 |
| 9 | t(6)1.40; m(4)2.4; m(2)3.2; m(4)4.3; m(1)4.7; m(3)7.3 |
| 10 | t(6)1.40; m(4)2.1; s(3)2.5; m(2)3.0; m(4)4.3; t(1)4.8; m(3)7.2–7.6 |
| 11 | t(6)1.40; m(4)2.4; m(5)3.2; m(4)4.3; m(1)4.6; m(3)7.1–8.0 |
| 12 | t(6)1.40; m(4)2.2; s(3)2.5; m(2)3.0; m(4)4.3; t(1)4.9; m(3)7.2–7.5 |
| 13 | t(6)1.40; m(4)2.5; s(3)3.1; m(2)3.3; m(4)4.2; t(1)4.8; m(3)7.0–8.0 |
| 14 | m(9)1.40; m(4)2.2; q(2)2.5; m(2)3.0; m(4)4.3; t(1)4.9; m(3)7.1–7.4 |
| 15 | m(12)1.40; m(4)2.2; m(3)3.0; m(4)4.2; t(1)4.8; m(3)7.1–7.3 |
| 16 | m(9)1.40; m(6)2.5; t(2)3.2; m(4)4.3; m(1)4.8; m(3)7.2–7.5 |
| 17 | m(15)1.40; m(4)2.4; m(2)3.1; m(5)4.3; m(3)7.3 |
| 18 | m(15)1.40; m(4)2.2; m(2)3.0; m(4)4.2; t(1)4.9; m(3)7.2–7.6 |
| 19 | t(6)1.40; m(6)2.2–3.1; m(5)4.5; m(4)7.4 |
| 20 | t(6)1.40; m(9)2.2–3.1; m(5)4.6; m(3)7.2–7.6 |
| 21 | t(6)1.30; m(4)2.2; s(3)2.3; m(2)3.0; m(4)4.3; t(1)4.9; m(3)7.2 |
| 22 | t(6)1.35; m(4)2.3; s(3)2.5; m(2)3.0; m(4)4.3; t(1)5.0; m(3)7.1 |
| 23 | m(9)1.40; m(8)2.1–3.3; m(5)4.3; m(3)7.2 |
| 24 | m(12)1.35; m(7)2.1–3.3; m(5)4.3; m(3)7.3 |
| 25 | m(12)1.40; m(4)2.2; m(2)3.0; m(6)4.5; m(3)6.6–7.2 |
| 26 | m(12)1.40; m(4)2.4; m(2)3.2; m(6)4.5; m(3)6.6–7.2 |
| 27 | t(6)1.30; m(4)2.2; m(2)3.0; m(5)3.8; m(8)7.4 |
| 28 | t(6)1.30; m(4)2.4; m(2)3.2; m(5)4.1; m(8)7.2 |
| 29 | m(6)1.40; m(4)2.3; s(3)2.6; m(2)3.0; m(5)4.2; m(3)7.5 |
| 30 | t(6)1.40; m(8)2.3; m(4)3.1; m(4)4.3; t(2)5.0; m(3)7.5 |
| 31 | t(6)1.40; m(4)2.2; m(2)3.1; s(3)3.75; m(4)4.2; t(1)4.9; m(3)6.7–7.1 |
| 32 | t(6)1.40; m(8)2.2; m(4)3.0; s(3)3.8; m(4)4.3; t(1)4.9; m(3)6.7–7.1 |
| 33 | t(6)1.30; m(8)2.2; s(3)2.5; m(4)3.1; m(4)4.2; t(1)5.0; m(2)7.3 |
| 34 | t(6)1.40; m(8)2.4; m(7)3.3; m(4)4.3; t(1)4.7; s(2)8.1 |

REMARKS
(1) s = singlet, d = doublet, t = triplet, q =

TABLE 2-continued

| Compound No. | NMR CHARACTERISTICS |
|---|---|
| | quartet and m = multiplet |
| (2) | The number in parenthesis represents the number of protons |
| (3) | The number following the parenthesis is the chemical shift in δ values |

EXAMPLE 3

Preparation of Pesticidal Compositions

Pesticidal compositions of Compound Nos. 1 to 34 were prepared by dissolving 0.3 g. of each of Compound Nos. 1 to 34 in 10 ml. of acetone to which four drops of a suitable wetting agent were added. This solution was further diluted with 100 ml. of water to provide a 3,000 ppm suspension. Additional compositions having a concentration of 1,000 ppm were formed by diluting an aliquot of the 3,000 ppm composition with water to obtain 1,000 ppm suspensions of the compounds. In a similar manner, still more dilute suspensions of 500 ppm, 200 ppm and 40 ppm compositions were prepared for some or all of these compounds.

EXAMPLE 4

Control of Southern Corn Rootworm

Five ml. of each of 500 ppm compositions of Compound Nos. 1 to 34 prepared in accordance with the procedure of Example 4 were pipetted onto a paper towel and inserted into a plastic bag. Two corn seedlings were also soaked in each of the 500 ppm compositions of Compound Nos. 1 to 34 and were also placed in the plastic bag. The bags were held for 18 hours before being loaded with 5 corn rootworm, *Diabrotica undecimpuntata*, larvae.

As a control, 5 ml. of water without the active compounds were pipetted onto a paper towel and inserted into a plastic bag. Two corn seedlings were also soaked with water and also placed in the plastic bag. The number of bags so prepared were equal in number to the number of bags of treated with the active compounds, Compound Nos. 1 to 34. After 18 hours, five corn rootworm larvae were, as in the case of the treated corn seedlings, loaded into each of the bags acting as controls.

After six days, the number of live larvae in each of the bags was noted. Percent control was calculated based on the number of live larvae in each of the bags treated with the active compounds of the present invention and compared to the number of live larvae in the control bags by methods well known in the art.

The results of this test are summarized in Table 3.

EXAMPLE 5

Control of Mites

Two cowpeas, in the first primary leaf stage, per pot, were sprayed with 1,000 ppm compositions of each of Compound Nos. 1–34 prepared in accordance with the procedure of Example 3. A spray atomizer was utilized to spray the plants such that the foilage was thoroughly drenched. Employing suitable controls, two replicates were used for each compound tested.

One day following this spraying step, a circle of tree tanglefoot was placed on the upper surface of the treated leaves and adult mites, *Tetranychus urticae* Koch, were transferred into this confinement.

Six days following infestation with mites, the plants were examined for adult live mites remaining on the leaves. On an estimated basis, in comparison with the number of living mites on the control plants, the percent control was determined.

The results of this test are tabulated in Table 3 below.

EXAMPLE 6

Control of Rice Planthopper

A plurality of pots each containing two rice seedling plants were treated with 1,000 ppm compositions, made in accordance with the procedures of Example 3, of each of Compound Nos. 1 to 34. The treatment took the form of spraying with a spray atomizer. Ten adult rice planthoppers, *Sogatodes oryzicola*, were placed on the plants in each pot one day following treatment. Similar treatment was afforded an equal number of pots each containing rice seedling plants untreated with the compositions of the present invention.

Five days after treatment, the number of surviving rice planthoppers on the plants treated with the compositions of the present invention were compared to the number of surviving rice planthoppers in the pots untreated with the compounds of the present invention. This comparison yielded a determination of percent control of rice planthoppers by Compound Nos. 1 to 34 by statistical methods well known in the art.

The results of this test are included in Table 3.

EXAMPLE 7

Control of Nematodes

Southern root-knot nematodes, *Meloidogyne incognita*, were reared in sandy culture soil using tomato as the host plant. Roots from the thus cultured plants were ground in a Waring [trademark] blender. Ground roots and culture soil were mixed with equal parts of unifested soil and the mixture placed in pots. Twenty-five ml. compositions of each of Compound Nos. 1 to 34 at 1,000 ppm concentration, were drenched into each pot containing 500 g. of the above described soil mixture. This resulted in a soil concentration of 50 ppm. An equal number of untreated pots were prepared.

One day after treatment, two tomato seedlings were planted in each of the test and control pots. Nineteen days after planting, the soil was washed from the roots. The treatments were evaluated by comparing the number of knots on plant roots from the treated nematode-infested soil to the number of knots on plant roots from the untreated nematode-infested control soil. This evaluation yielded percent control by each of Compound Nos. 1 to 34.

The results of this test are also set forth in Table 3.

TABLE 3

| Compound No. | Percent Pesticidal Control | | | |
|---|---|---|---|---|
| | CR at 500 ppm | MI at 1000 ppm | NE at 50 ppm | RP at 1000 ppm |
| 1 | 80 | 0 | 0 | 0 |
| 2 | 100 | 60 | 80 | 0 |
| 3 | 100 | 50 | 0 | 0 |
| 4 | 100 | 50 | 0 | 0 |
| 5 | 100 | 40 | 50 | 90 |
| 6 | 100 | 80 | 0 | 50 |
| 7 | 100 | 100 | 0 | 75 |
| 8 | 100 | 50 | 0 | 50 |
| 9 | 100 | 80 | 30 | 0 |
| 10 | 100 | 0 | 30 | 95 |
| 11 | 100 | 0 | 100 | 100 |
| 12 | 100 | 0 | 95 | 100 |
| 13 | 100 | 0 | 0 | 100 |
| 14 | 100 | 0 | 30 | 100 |
| 15 | 100 | 0 | 0 | 0 |
| 16 | 100 | 0 | 0 | 0 |
| 17 | 100 | 90 | 0 | 0 |
| 18 | 100 | 0 | 98 | 0 |
| 19 | 100 | 30 | 50 | 0 |
| 20 | 100 | 0 | 90 | 0 |
| 21 | 100 | 0 | 50 | 0 |
| 22 | 100 | 90 | 20 | 0 |
| 23 | 100 | 0 | 0 | 0 |
| 24 | 100 | 0 | 70 | 0 |
| 25 | 100 | 0 | 0 | 30 |
| 26 | 100 | 0 | 70 | 0 |
| 27 | 100 | 0 | 0 | 0 |
| 28 | 100 | 100 | 80 | 0 |
| 29 | 100 | 95 | 100 | 0 |
| 30 | 100 | 0 | 0 | 0 |
| 31 | 100 | 0 | 0 | 90 |
| 32 | 100 | 0 | 0 | 30 |
| 33 | 100 | 0 | 0 | 100 |
| 34 | 100 | 0 | 0 | 40 |

Footnotes
CR = Corn Rootworm
MI = Mites
NE = Nematodes
RP = Rice Planthopper

EXAMPLE 8

Systemic Control of Rice Planthopper

Compositions of Compound Nos. 10 and 11 were prepared to a concentration of 200 ppm in accordance with the procedure of Example 3.

Thirty ml. of the 200 ppm suspension compositions of Compound Nos. 10 and 11 were syringe injected under the root system of two rice seedling plants in a pot containing 600 g. of potting soil. The thus resulting soil concentration of Compound Nos. 10 and 11 was 10 ppm. Similar pots containing two rice seedling plants containing 570 grams of potting soil was similarly prepared without treatment with the 200 ppm compositions of Compound Nos. 10 and 11. These untreated pots were used as controls.

One day after treatment 10 adult rice planthoppers, *Sogatodes oryzicola*, were placed on the plants in each of the pots. The planthoppers were confined to the plants by plastic cylinders. A comparison of the number of surviving planthoppers on the treated and untreated pots five days after their loading on the plants was used to determine percent control of rice planthopper.

The results of this systemic control test are tabulated in Table 4.

TABLE 4

| | Systemic Control of Rice Planthoppers | |
|---|---|---|
| Compound No. | Concentration, ppm. | Percent Control of Rice Planthoppers |
| 10 | 10 | 84 |
| 11 | 10 | 100 |

EXAMPLE 9

Control of Southern Corn Rootworm in Soil

Compositions containing 40 ppm suspensions of Compound Nos. 2, 5, 6 and 25, prepared in accordance with the method used in Example 3, were added to plastic pots holding 300 g. of soil. Each of the treated pots were treated with 30 ml. of the 40 ppm suspension compositions to provide a resulting soil concentration of 4 ppm. Thereafter, two corn seedlings were placed in each pot. Two corn seedlings were similarly planted in 300 g. of soil in additional pots not treated with Compound Nos. 2, 5, 6 and 25.

One week after planting, each pot, treated and untreated, was loaded with 10 corn rootworm larvae. One week after corn rootworm infestation the pots were emptied into a tray containing salt water solution and the surviving larvae were collected from the water on a fine mesh screen and counted. The number of surviving larvae in the treated pots compared to the number of surviving larvae in the untreated pots resulted in a determination of percent control by methods known to those skilled in the art.

A tabulation of the results of this test appears in Table 5.

TABLE 5

| | Soil Control of Corn Rootworm | |
|---|---|---|
| Compound No. | Soil Concentration, ppm. | Percent Control of Corn Rootworm |
| 2 | 4 | 89 |
| 5 | 4 | 81 |
| 6 | 4 | 100 |
| 25 | 4 | 90 |

The above embodiments and examples are given to illustrate the scope and spirit of the instant invention. These embodiments and examples will make apparent, to those skilled in the art, other embodiments and examples. These other embodiments and examples are within the contemplation of the present invention. Therefore, the scope of the present invention should be limited only by the appended claims.

What is claimed is:

1. A compound having the structural formula

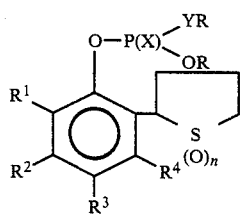

where
R is $C_1$-$C_6$ alkyl;
$R^1$ to $R^4$ are the same or different and are hydrogen, halogen, nitro, $C_1$-$C_8$ alkyl, $C_1$-$C_2$ haloalkyl, $C_5$-$C_6$ cycloalkyl, $C_1$-$C_3$ aralkyl, phenyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_3$ alkoxy substituted phenyl, phenoxy, phenylthio, phenylsulfonyl, phenylsulfinyl, tetrahydro-2-thienyl, dioxytetrahydro-2-thienyl, $C_2$-$C_5$ alkoxycarbonyl or $N(R^5,R^6)$;
$R^5$ and $R^6$ are the same or different and are hydrogen or $C_1$-$C_2$ alkyl;
X and Y are the same or different and are oxygen or sulfur; and
n is 0, 1 or 2.

2. A compound in accordance with claim 1 wherein
R is $C_1$-$C_2$ alkyl;
$R^1$ is hydrogen, $C_1$-$C_6$ alkoxy, $C_2$-$C_5$ alkoxycarbonyl, phenyl, thienyl, dioxothienyl or chlorine;
$R^2$ is hydrogen or methyl;
$R^3$ is hydrogen, methyl, ethyl, isopropyl, methoxy, isopropyloxy, nitro, chlorine, methylthio, methylsulfinyl, methylsulfonyl or phenyl;
$R^4$ is hydrogen or methyl;
X is sulfur;
Y is oxygen; and
n is 0 or 2.

3. A compound in accordance with claim 2 wherein
R is ethyl;
$R^1$ is hydrogen or chlorine; and
$R^3$ is methyl, methoxy, nitro, chlorine, methylthio, methylsulfinyl or methylsulfonyl.

4. A pesticidal composition comprising a pesticidally effective amount of the compound of claim 1 and a carrier therefor.

5. An insecticidal composition comprising an insecticidally effective amount of the compound of claim 1 and a carrier therefor.

6. A nematocidal composition comprising a nematocidally effective amount of the compound of claim 1 and a carrier therefor.

7. An acaricidal composition comprising an acaricidally effective amount of the compound of claim 1 and a carrier therefor.

8. A method of controlling pests comprising applying a pesticidally effective amount of the compound of claim 1 to the locus to be protected.

9. A method of controlling insects comprising applying an insecticidally effective amount of the compound of claim 1 to the locus to be protected.

10. A method in accordance with claim 9 wherein said insect is Southern Corn Rootworm or Rice Planthopper.

11. A method in accordance with claim 10 wherein said locus to be protected is the soil around the roots of corn plants.

12. A method of controlling nematodes comprising applying a nematocidally effective amount of the compound of claim 1 to the locus to be protected.

13. A method of controlling acarids comprising applying an acaricidally effective amount of the compound of claim 1 to the locus to be protected.

* * * * *